United States Patent [19]

Seele et al.

[11] Patent Number: 5,057,532

[45] Date of Patent: Oct. 15, 1991

[54] AZOLYLETHYLCYCLOPROPANES AND THEIR USE THEREOF AS CROP PROTECTION AGENTS

[75] Inventors: Rainer Seele; Reiner Kober, both of Fussgoenheim; Eberhard Ammermann, Ludwigshafen; Gisela Lorenz, Neustadt; Johann Jung; Wilhelm Rademacher, both of Limburgerhof, all of Fed. Rep. of Germany

[73] Assignee: BASF Aktiengesellschaft, Ludwigshafen, Fed. Rep. of Germany

[21] Appl. No.: 483,674

[22] Filed: Feb. 23, 1990

[30] Foreign Application Priority Data

Mar. 25, 1989 [DE] Fed. Rep. of Germany ....... 3909862

[51] Int. Cl.$^5$ ................. A01N 43/653; C07D 249/08
[52] U.S. Cl. ..................... 514/383; 514/184; 548/267.8; 548/268.6; 71/76; 71/92
[58] Field of Search ............ 71/76, 92; 514/184, 514/383; 548/267.8, 268.6

[56] References Cited

U.S. PATENT DOCUMENTS

| | | | |
|---|---|---|---|
| 4,719,307 | 1/1988 | Lantzsch et al. | 548/267.8 |
| 4,913,727 | 4/1990 | Stroech et al. | 548/267.8 |
| 4,923,502 | 5/1990 | Elliott et al. | 548/267.8 |

FOREIGN PATENT DOCUMENTS

| | | |
|---|---|---|
| 212605 | 3/1987 | European Pat. Off. . |
| 2064520 | 6/1981 | United Kingdom ............ 548/267.8 |

Primary Examiner—Patricia L. Morris
Attorney, Agent, or Firm—Oblon, Spivak, McClelland, Maier & Neustadt

[57] ABSTRACT

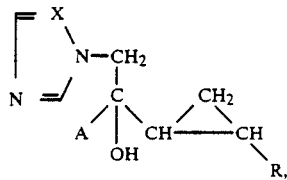

where A is $C_1$-$C_6$-alkyl, $C_3$-$C_6$-cycloalkyl, $C_3$-$C_6$-cycloalkenyl or tetrahydropyranyl, each of which is unsubstituted or mono- to trisubstituted by halogen, nitro, phenoxy, amino, alkyl or haloalkyl having 1 to 4 carbon atoms in each case, and X is N, and their acid addition salts and metal complexes which are tolerated by plants, and fungicides and growth regulators containing these compounds.

7 Claims, No Drawings

AZOLYLETHYLCYCLOPROPANES AND THEIR USE THEREOF AS CROP PROTECTION AGENTS

The present invention relates to novel azole compounds, the preparation thereof and fungicides and growth regulators containing these.

The use of E-1-[1-(4-chlorophenyl)-1-hydroxy-2-(1,2,4-triazol-1-yl)ethyl]-2-phenylcyclopropane as a fungicide and growth regulator has been disclosed (EP 212 605). However, the fungicidal and growth-regulatory effects are not satisfactory in all cases.

We have now found that compounds of the formula

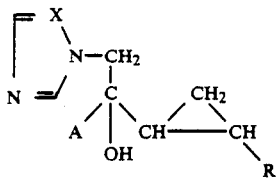

where A and R are identical or different and each is $C_1$–$C_6$-alkyl, $C_3$–$C_6$-cycloalkyl, $C_3$–$C_6$-cycloalkenyl, tetrahydropyranyl, pyridyl or phenyl, each of which can be substituted one to three times by halogen, nitro, phenoxy, amino, alkyl or haloalkyl having 1 to 4 carbons in each case, with the proviso that A and R are not both phenyl, X is CH or N,
and their acid addition salts or metal complexes which are tolerated by plants have a better fungicidal and growth-regulatory effect than known azole compounds.

The compounds of the formula I contain chiral centers and are generally obtained in the form of mixtures of diastereomers. The diastereomers of the compounds according to the invention can be separated and isolated in pure form in a conventional manner, for example on the basis of differences in solubility or by column chromatography. Pure enantiomers can be obtained by conventional methods from diastereomers isolated in such ways. Both the pure diastereomers or enantiomers and the mixtures thereof produced in the synthesis can be used as fungicides and growth regulators.

The present invention embraces all these compounds and mixtures thereof.

Examples of A and R are methyl, ethyl, isopropyl, n-propyl, n-butyl, sec-butyl, tert.-butyl, n-pentyl, neopentyl, hexyl, trifluoromethyl, trichloromethyl, phenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, 2-methoxyphenyl, 3-methoxyphenyl, 4-methoxyphenyl, 2,4-dimethoxyphenyl, 4-ethylphenyl, 4-isopropylphenyl, 4-tert.-butylphenyl, 4-tert.-butyloxyphenyl, 2-chloro-4-fluorophenyl, 2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-trifluoromethylphenyl, 3-trifluoromethylphenyl, 4-trifluoromethylphenyl, cyclopropyl, cyclobutyl, cyclopentyl, cyclohexyl, tetrahydropyranyl, 2-cyclohexenyl, 3-cyclohexenyl and pyridyl.

Examples of acid addition salts are the hydrochlorides, hydrobromides, sulfates, nitrates, phosphates, oxalates or dodecylbenzenesulfonates. The activity of the salts derives from the cation so that the nature of the anion is generally immaterial. The salts of the active ingredients according to the invention are prepared by reacting the azolylethylcyclopropanes I with suitable acids.

Metal complexes of the active ingredients I or salts thereof can be formed, for example, with copper, zinc, tin, manganese, iron, cobalt or nickel, by reacting the azolylethylcyclopropanes with appropriate metal salts, e.g. with copper sulfate, zinc chloride, tin chloride, manganese sulfate or iron sulfate.

The compounds of the formula I can be prepared by reacting a compound of the formula II

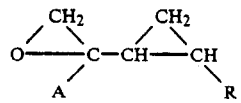

where A and R have the abovementioned meanings, with a compound of the formula III

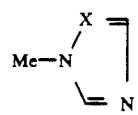

where Me is hydrogen or a metal, and X has the abovementioned meaning.

Where Me is hydrogen the reaction is carried out, for example, in the presence or absence of a solvent or diluent, with or without the addition of an inorganic or organic base and of a reaction accelerator at from 10° to 120° C. The preferred solvents and diluents include ketones such as acetone, methyl ethyl ketone or cyclohexanone, nitriles such as acetonitrile or propionitrile, alcohols such as methanol, ethanol, iso-propanol, n-butanol or glycol, esters such as ethyl acetate, methyl acetate or butyl acetate, ethers such as tetrahydrofuran, diethyl ether, dimethoxyethane, dioxane or diisopropyl ether, amides such as dimethylformamide, dimethylacetamide or N-methylpyrrolidone, and dimethyl sulfoxide, sulfolane or mixtures thereof.

Examples of suitable bases, which can also be used as acid-binding agents in the reaction, are alkali metal hydroxides such as lithium, sodium or potassium hydroxide, alkali metal carbonates such as sodium, potassium or cesium carbonate or sodium, potassium or cesium bicarbonate, pyridine or 4-dimethylaminopyridine. However, it is also possible to use other conventional bases.

Suitable and preferred reaction accelerators are metal halides such as sodium iodide or potassium iodide, quaternary ammonium salts such as tetrabutylammonium chloride, bromide, iodide or bisulfate, benzyltriethylammonium chloride or bromide or crown ethers such as 12-crown-4, 15-crown-5, 18-crown-6, dibenzo-18-crown-6 or dicyclohexano-18-crown-6.

The reaction is generally carried out at from 20° to 150° C., preferably from 20° to 120° C., under atmospheric or superatmospheric pressure, continuously or batchwise.

If Me is a metal, the reaction is carried out in the presence or absence of a solvent or diluent and with or without the addition of a strong inorganic or organic base, generally at from −10° to 120° C. The preferred solvents and diluents include amides such as dimethylformamide, diethylformamide, dimethylacetamide, diethylacetamide, N-methylpyrrolidone, hexamethylphosphoric triamide, sulfoxides such as dimethyl sulfoxide and, finally, sulfolane.

Examples of suitable bases, which can also be used as acid-binding agents in the reaction, are alkali metal hydrides such as lithium, sodium and potassium hydride, alkali metal amides such as those of sodium and potassium, and sodium or potassium tert.-butoxide, triphenylmethyllithium, -sodium or -potassium, and naphthyllithium, -sodium or -potassium.

The starting compounds II can be prepared, for example, by reacting an unsaturated ketone of the formula

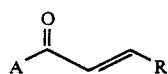

where A and R have the abovementioned meanings, with two equivalents of the sulfur ylide V

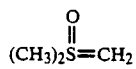

(cf. Corey, Chaykovsky, J. Am. Chem. Soc. 64 (1962) 3782).

The compounds of the formula IV can be prepared by conventional processes for synthesizing olefins (cf., for example, Houben-Weyl-Müller, Methoden der organischen Chemie, Georg Thieme Verlag, Stuttgart 1972, vol. V, 1b).

The Examples which follow illustrate the preparation of the active ingredients.

I. PREPARATION OF THE STARTING SUBSTANCES

Example A 87.5 g of 2,4-dichlorobenzaldehyde are added slowly to a solution of 50 g of pinacolone in 200 ml of ethanol and 1 ml of sodium hydroxide solution (50% by weight), keeping the internal temperature at 30° C. or below. The mixture is stirred at 20° C. for 24 hours and then the precipitate is filtered off with suction and dried. 105.5 g (82%) of tert-butyl 2,4-dichlorostyryl ketone are obtained.

Example B 90 g of tert-butyl 2,4-dichlorostyryl ketone are dissolved in 200 ml of dimethylformamide and, at 0° C. under a nitrogen atmosphere, 86.9 g of trimethylsulfoxonium iodide are added. Then 44.2 g of potassium tert-butylate are rapidly added and the mixture is heated to 60° C. The solution is stirred at 60° C. for 3 days and then 200 ml of water are added and the mixture is extracted several times with methyl tert-butyl ether. The isolated organic phase is washed twice with water and then dried over sodium sulfate and concentrated, resulting in 69.8 g (70%) of trans-1-(2-tert-butyl-2-oxiranyl)-2-(2,4-dichlorophenyl)cyclopropane.

II. PREPARATION OF THE FINAL PRODUCTS

Example 1

5.6 g of sodium hydroxide (50% by weight) are added to a solution of 5.1 g of triazole in 50 ml of N-methylpyrrolidone, and the mixture is heated at 50° C. for 30 minutes. Then, at room temperature, 10 g of trans-1-(2-tert-butyl-2-oxiranyl)-2-(2,4-dichlorophenyl)cyclopropane which is dissolved in 50 ml of N-methylpyrrolidone are slowly added dropwise. The reaction mixture is stirred at room temperature for 18 hours and then 100 ml of water are added to the solution and the mixture is extracted several times with methyl tert-butyl ether. The isolated organic phase is washed twice with water and then dried over sodium sulfate and concentrated. The remaining residue is purified by flash chromatography on silica gel (9:1 ethyl acetate/n-hexane), resulting in separation of the diastereomers. 7.4 g (60% overall yield) of trans-1-[1-tert-butyl-1-hydroxy-2-(1,2,4-triazol-1-yl)ethyl]-2-(2,4-dichlorophenyl)cyclopropane are obtained.

Diastereomer A; melting point 151°–158° C. (compound no. 1)

Diastereomer B; melting point 98°–101° C. (compound no. 2)

The compounds listed in the Table can be prepared as in Example 1.

TABLE

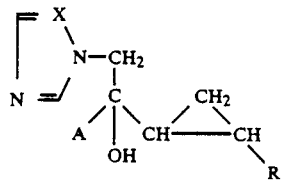

| Ex. no. | A | B | X | mp/IR | Isomer |
|---|---|---|---|---|---|
| 1 | tert.-$C_4H_9$ | 2,4-$Cl_2$—$C_6H_3$ | N | 151–153° C. | Diastereomer 1 |
| 2 | tert.-$C_4H_9$ | 2,4-$Cl_2$—$C_6H_3$ | N | 98–101° C. | Diastereomer 2 |
| 3 | tert.-$C_4H_9$ | 2,4-$Cl_2$—$C_6H_3$ | N | 163–167° C. | $D_1:D_2 = 3:2$ |
| 4 | tert.-$C_4H_9$ | 2-Cl—$C_6H_4$ | N | | |
| 5 | tert.-$C_4H_9$ | 2-Cl—$C_6H_4$ | CH | | |
| 6 | tert.-$C_4H_9$ | 4-Cl—$C_6H_4$ | N | 193–198° C. | Diastereomer 1 |
| 7 | tert.-$C_4H_9$ | 4-Cl—$C_6H_4$ | N | 111–113° C. | Diastereomer 2 |
| 8 | tert.-$C_4H_9$ | 4-Cl—$C_6H_4$ | CH | 147–148° C. | $D_1:D_2 = 2:1$ |
| 9 | tert.-$C_4H_9$ | 2-Cl-4-F—$C_6H_3$ | N | | |
| 10 | tert.-$C_4H_9$ | 2-$CF_3$—$C_6H_4$ | N | | |
| 11 | tert.-$C_4H_9$ | 4-$CF_3$—$C_6H_4$ | N | | |
| 12 | tert.-$C_4H_9$ | 2-F—$C_6H_4$ | N | | |
| 13 | tert.-$C_4H_9$ | 4-F—$C_6H_4$ | N | | |
| 14 | tert.-$C_4H_9$ | 2,4-$F_2$—$C_6H_3$ | N | | |
| 15 | tert.-$C_4H_9$ | 2-Br—$C_6H_4$ | N | | |
| 16 | tert.-$C_4H_9$ | 4-Br—$C_6H_4$ | N | | |
| 17 | tert.-$C_4H_9$ | $C_6H_5$ | N | | |

TABLE-continued $$\begin{array}{c} X \\ | \\ N-CH_2 \\ | \\ N=\overset{\displaystyle |}{\underset{\displaystyle |}{C}}-\overset{\displaystyle CH_2}{\underset{\displaystyle CH}{\diagdown}}\overset{\displaystyle |}{\underset{\displaystyle R}{CH}} \\ A \quad OH \end{array}$$

| Ex. no. | A | B | X | mp/IR | Isomer |
|---|---|---|---|---|---|
| 18 | tert.-$C_4H_9$ | 2-$C_{10}H_7$ | N | | |
| 19 | tert. $C_4H_9$ | 4-$C_{12}H_9$ | N | | |
| 20 | tert.-$C_4H_9$ | 2-$CH_3$—$C_6H_4$ | N | | |
| 21 | tert.-$C_4H_9$ | 2-$OCH_3$—$C_6H_4$ | N | 131–135° C. | Diastereomer 1 |
| 22 | tert.-$C_4H_9$ | ![tetrahydropyranyl] | N | | |
| 23 | $CH_3$ | 2-Cl—$C_6H_4$ | N | | |
| 24 | $CH_3$ | 4-Cl—$C_6H_4$ | N | | |
| 25 | $CH_3$ | 2,4-$Cl_2$—$C_6H_3$ | N | | |
| 26 | $CH_3$ | 2-$CF_3$—$C_6H_4$ | N | | |
| 27 | $CH_3$ | 2-Br—$C_6H_4$ | N | | |
| 28 | cyclopropyl | 2-Cl—$C_6H_4$ | N | | |
| 29 | cyclopropyl | 3-Cl—$C_6H_4$ | N | | |
| 30 | cyclopropyl | 4-Cl—$C_6H_4$ | N | 108–110° C. | $D_1:D_2 = 6:1$ |
| 31 | cyclopropyl | 4-Cl—$C_6H_4$ | N | resin | $D_1:D_2 = 3:2$ |
| 32 | cyclopropyl | 4-Cl—$C_6H_4$ | CH | | |
| 33 | cyclopropyl | 2,4-$Cl_2$—$C_6H_3$ | N | | |
| 34 | cyclopropyl | 4-F—$C_6H_4$ | N | | |
| 35 | cyclopropyl | 2-$CF_3$—$C_6H_4$ | N | | |
| 36 | cyclopropyl | 4-$NO_2$—$C_6H_4$ | N | | |
| 37 | cyclopropyl | 4-$NH_2$—$C_6H_4$ | N | | |
| 38 | cyclopropyl | p-$C_6H_5$—O—$C_6H_4$ | N | | |
| 39 | cyclopropyl | 2-$C_{10}H_7$ | N | | |
| 40 | cyclohexyl | 2-Cl—$C_6H_4$ | N | | |
| 41 | cyclohexyl | 3-Cl—$C_6H_4$ | N | | |
| 42 | cyclohexyl | 4-Cl—$C_6H_4$ | N | 138–140° C. | $D_1:D_2 = 3:1$ |
| 43 | cyclohexyl | 2-F—$C_6H_4$ | N | | |
| 44 | cyclohexyl | 2-$CF_3$—$C_6H_4$ | N | | |
| 45 | $C_6H_5$ | cyclopropyl | N | | |
| 46 | $C_6H_5$ | cyclopropyl | N | | |
| 47 | $C_6H_5$ | ![tetrahydropyranyl] | N | | |
| 48 | 4-Cl—$C_6H_4$ | cyclopropyl | N | | |
| 49 | 4-Cl—$C_6H_4$ | cyclohexyl | N | | |
| 50 | 4-Cl—$C_6H_4$ | 2-cyclohexenyl | N | | |
| 51 | 4-Cl—$C_6H_4$ | 3-cyclohexenyl | N | | |
| 52 | 4-Cl—$C_6H_4$ | ![tetrahydropyranyl] | N | | |
| 53 | 2,4-$Cl_2$—$C_6H_3$ | cyclopentyl | N | | |
| 54 | 2,4-$Cl_2$—$C_6H_3$ | cyclohexyl | N | | |
| 55 | 4-F—$C_6H_4$ | cyclopropyl | N | | |
| 56 | 4-F—$C_6H_4$ | cyclopentyl | N | | |
| 57 | 4-F—$C_6H_4$ | cyclohexyl | N | | |
| 58 | 4-F—$C_6H_4$ | 2-cyclohexenyl | N | | |
| 59 | 4-$OCH_3$—$C_6H_4$ | cyclopropyl | N | | |
| 60 | 4-$OCH_3$—$C_6H_4$ | cyclohexyl | N | | |
| 61 | 4-$OCH_3$—$C_6H_4$ | 3-cyclohexenyl | N | | |
| 62 | 4-$OCH_3$—$C_6H_4$ | $CCl_3$ | N | | |
| 63 | 4-$OCH_3$—$C_6H_4$ | $CCl_3$ | CH | | |
| 64 | 3-pyridyl | tert.-$C_4H_9$ | N | 132–134° C. | $D_1:D_2 = 4:1$ |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The application rates of the fungicidal agents depends on the type of effect desired, and varies from 0.02 to 3 kg of active ingredient and more. The novel active ingredients may also be used for protecting materials, e.g., against *Paecilomyces variotii*.

The novel compounds may exercise a variety of influences on practically all plant development stages, and are therefore used as growth regulators. The diversity of action of growth regulators depends especially on a) the type and variety of plant;
b) the time applied, with reference to the development stage of the plants and the time of the year;
c) the place and method of application (seed treatment, soil treatment, or application to foliage);
d) climatic factors, e.g., average temperature, amount of precipitate, sunshine and duration;
e) soil conditions (including fertilization);
f) the formulation of the active ingredient; and
g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

Of practical importance is the reduction in vegetative growth in fruit trees and other woody plants, thus saving pruning costs.

The use of growth regulators is also important for inhibiting plant height and changing the time of ripening in cotton. It is thus possible for this important crop to be harvested completely mechanically.

Growth regulators may also increase or inhibit lateral branching. This is of interest when, for instance in tobacco plants, it is desired to inhibit the formation of lateral shoots (suckers) in favor of leaf development.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with the novel agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The azolylethylcyclopropanes of the formula I may raise the yield by influencing plant metabolism or by promoting or inhibiting vegetative and/or generative plant growth.

C. It is also possible with compounds I according to the invention to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with azolylethylcyclopropanes. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia, the size of the stomata opening is reduced;
a thicker epidermis and cuticle are formed;
penetration of the soil by the roots is improved;
the micro-climate in the stand is favorably influenced by the more compact growth.

The active ingredients according to the invention may be applied not only to the seed (as a disinfectant), but also to the soil, i.e., via the roots, and to the foliage by spraying.

As a result of the good tolerance by crop plants, the application rate when the active ingredients are used as growth regulators may vary within wide limits.

When the active ingredients are used for treating seed, amounts of from 0.001 to 50, and preferably from 0.005 to 0.5, g per kg of seed are generally required. For foliage and soil treatment, amounts of from 0.01 to 10, and preferably from 0.05 to 1, kg/ha are generally considered to be sufficient.

The agents based on azolylethylcyclopropanes can be used as conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene, toluene), chlorinated aromatics (e.g., chlorobenzenes), paraffins (e.g., crude oil fractions), alcohols (e.g., methanol, butanol), amines (e.g., ethanolamine), N,N-dimethylformamide, and water; carriers such as ground natural minerals (e.g., kaolins, aluminas, talc and chalk) and ground synthetic minerals (e.g., highly disperse silica and silicates); emulsifiers and other surfactants, such as nonionic and anionic emulsifiers (e.g., polyoxyethylene fatty alcohol ethers, alkyl sulfonates); and dispersants such as lignin, sulfite waste liquors and methylcellulose. The agents according to the invention are preferably employed in aqueous solution with or without the addition of water-miscible organic solvents such as methanol or other lower alcohols, acetone, N,N-dimethylformamide or N-methylpyrrolidone.

The fungicidal agents generally contain from 0.1 to 95, and preferably from 0.5 to 90, wt % of active ingredient.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 2 is mixed with 10 parts by weight of N-methyl-α-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 2 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 2 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 2 is intimately mixed with 97 parts by weight of particulate kaolin. A dust is obtained containing 3% by weight of the active ingredient.

VII. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 2 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 2 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum. When the compounds according to the invention are mixed with growth regulators, synergistic effects also often occur.

USE EXAMPLES

For comparison purposes, E-1-[1-(4-chlorophenyl)-1-hydroxy-(1,2,4-triazol-1-yl)-1-ethyl]-2-phenylcyclopropane (A) disclosed in EP 212,605 was used.

USE EXAMPLE 1

Action on *Botrytis Cinerea* in Pimientos

Pimiento seedlings of the "Neusiedler Ideal Elite" variety with 4 to 5 well developed leaves were sprayed to runoff with aqueous suspensions containing (dry basis) 80% of active ingredient and 20% of emulsifier. After the sprayed-on layer had dried, the plants were sprayed with a conidial suspension of the fungus *Botrytis cinerea* and kept in a high-humidity chamber at 22° to 24° C. After 5 days, the disease had spread on the untreated control plants to such an extent that the necroses covered the major portion of the leaves.

The results show that active ingredients 3, 6 and 31, applied as 0.05 wt % spray liquors, had a better fungicidal action (95%) than prior art comparative agent A (40%).

USE EXAMPLE 2

Action on *Pyricularia Oryzae* (Protective)

Leaves of pot-grown rice seedlings of the "Bahia" variety were sprayed to runoff with aqueous emulsions consisting (dry basis) of 80% of active ingredient and 20% of emulsifier, and inoculated 24 hours later with an aqueous spore suspension of *Pyricularia oryzae*. The plants were then set up in climatic cabinets at from 22° to 24° C. and a relative humidity of 95 to 99%. The extent of fungus spread was assessed after 6 days.

The results show that active ingredients 6 and 8, applied as 0.05 wt % spray liquors, had a better fungicidal action (90%) than prior art comparative agent A (65%).

To determine the growth-regulating properties of the candidate compounds, the test plants were grown in plastic pots (approx. 12.5 cm in diameter, and having a volume of about 500 ml) in a substrate provided with sufficient nutrients.

In the preemergence treatment method, the candidate compounds were sprayed as aqueous formulations onto the seedbed on the day of sowing.

In the postemergence method, the compounds were sprayed as aqueous formulations onto the plants. The growth-regulating action observed was confirmed at the end of the experiment by measuring the height of the plants. The figures obtained were compared with the growth height of the untreated plants. The prior art active ingredient chlorocholine chloride (B) and the active ingredient of Example 15 of EP-212,605 were used for comparison purposes.

The reduction in growth height was also accompanied by a deeper leaf coloration. The increased chlorophyll content is indicative of an increased rate of photosynthesis, making for bigger yields.

The individual data are given in the following tables.

Comparative substances:

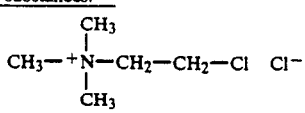

B

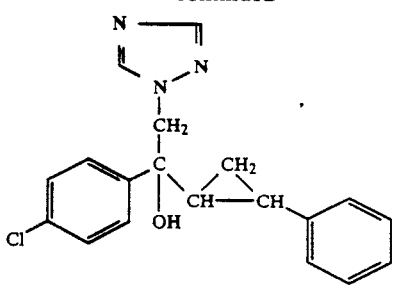

A

USE EXAMPLE 3

Spring Barley, "Aramir" Variety

Preemergence (Soil) Treatment

| Active Ingr. No. | Concentration mg of a.i./vessel | Growth height relative |
|---|---|---|
| untreated | — | 100 |
| B | 6 | 80.0 |
| A | 6 | 94.7 |
| 1 | 6 | 45.8 |
| 6 | 6 | 42.5 |
| 30 | 6 | 39.2 |
| 31 | 6 | 55.5 |

USE EXAMPLE 4

Spring Rape, "Petranova" Variety

Preemergence (Soil) Treatment

| Active Ingredient Nr. | Concentration mg of a.i./vessel | Growth height relative |
|---|---|---|
| untreated | — | 100 |
| B | 6 | 92.7 |
| A | 6 | 100.0 |
| 1 | 6 | 18.1 |
| 3 | 6 | 76.6 |
| 6 | 6 | 26.2 |
| 8 | 6 | 74.6 |
| 30 | 6 | 18.2 |
| 31 | 6 | 24.2 |

USE EXAMPLE 5

Spring Rape, "Petranova" Variety

Postemergence (Leaf) Treatment

| Active Ingredient Nr. | Concentration mg of a.i./vessel | Growth height relative |
|---|---|---|
| untreated | — | 100 |
| B | 6 | 93.2 |
| A | 6 | 85.0 |
| 1 | 6 | 60.8 |
| 2 | 6 | 74.9 |
| 3 | 6 | 74.9 |
| 6 | 6 | 64.8 |
| 8 | 6 | 72.9 |

We claim:

1. A triazolylethylcyclopropane of the formula I

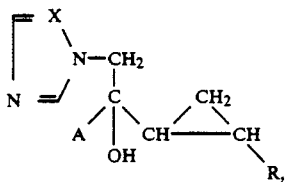

where A is $C_1$–$C_6$-alkyl, $C_3$–$C_6$-cycloalkyl, $C_3$–$C_6$-cycloalkenyl or tetrahydropyranyl, and where R is phenyl, and each of the A and R groups is unsubstituted or mono- to trisubstituted by halogen, nitro, phenoxy, amino, alkyl or haloalkyl having 1 to 4 carbon atoms in each case, and X is N, and their acid addition salts and metal complexes which are tolerated by plants.

2. A triazolylethylcyclopropane of the formula I as set forth in claim 1, where A is tert-butyl and R is phenyl which is unsubstituted or bears one or two substituents selected from the group consisting of fluorine, chlorine, bromine and trifluoromethyl.

3. A fungicidal composition containing a carrier and a fungicidally effective amount of a triazolylethylcyclopropane of the formula I

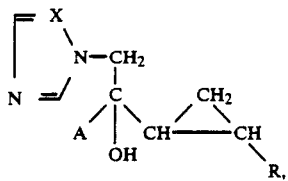

where A is $C_1$–$C_6$-alkyl, $C_3$–$C_6$-cycloalkyl, $C_3$–$C_6$-cycloalkenyl or tetrahydropyranyl, and where R is phenyl, and each of the A and R groups is unsubstituted or mono- to trisubstituted by halogen, nitro, phenoxy, amino, alkyl or haloalkyl having 1 to 4 carbon atoms in each case, and X is N, or an acid addition salts or metal complexes thereof tolerated by plants.

4. A process for combating fungi, wherein a fungicidally effective amount of a triazolylethylcyclopropane of the formula I

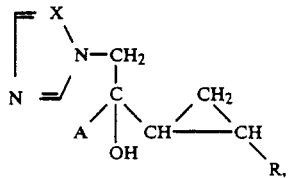

where A is $C_1$–$C_6$-alkyl, $C_3$–$C_6$-cycloalkyl, $C_3$–$C_6$-cycloalkenyl or tetrahydropyranyl, and where R is phenyl, and each of the A and R groups is unsubstituted or mono- to trisubstituted by halogen, nitro, phenoxy, amino, alkyl or haloalkyl having 1 to 4 carbon atoms in each case, and X is N, or an acid addition salt or metal complex thereof tolerated by plants is allowed to act on the fungi, or the soil, plants or seed threatened by fungus attack.

5. A compound of the formula I as set forth in claim 1, where A is tert-butyl, R is 2,4-dichlorophenyl and X is N.

6. A compound of the formula I as set forth in claim 1, where A is tert-butyl, R is 4-chlorophenyl and X is N.

7. A compound of the formula I as set forth in claim 1, where A is cyclopropyl, R is 4-chlorophenyl and X is N.

* * * * *